United States Patent
Wang et al.

(10) Patent No.: US 11,351,192 B2
(45) Date of Patent: Jun. 7, 2022

(54) DE-COLONIZATION DRUG, PREPARATION METHOD THEREFOR, AND APPLICATION THEREOF

(71) Applicant: BEIJING HYGIENE & HEALTHCARE INNOVATION TECHNOLOGY CO., LTD., Beijing (CN)

(72) Inventors: Zhengwang Wang, Beijing (CN); Gangyi Li, Beijing (CN)

(73) Assignee: BEIJING HYGIENE & HEALTHCARE INNOVATION TECHNOLOGY CO., LTD., Beijing (CN)

( * ) Notice: Subject to any disclaimer, the term of this patent is extended or adjusted under 35 U.S.C. 154(b) by 9 days.

(21) Appl. No.: 16/496,669

(22) PCT Filed: Aug. 25, 2017

(86) PCT No.: PCT/CN2017/099032
§ 371 (c)(1),
(2) Date: Sep. 23, 2019

(87) PCT Pub. No.: WO2019/037079
PCT Pub. Date: Feb. 28, 2019

(65) Prior Publication Data
US 2020/0376023 A1    Dec. 3, 2020

(51) Int. Cl.
*A61K 33/20* (2006.01)
*A61P 31/04* (2006.01)
*A61K 31/19* (2006.01)
*A61K 31/194* (2006.01)
*A61K 33/06* (2006.01)

(52) U.S. Cl.
CPC .............. *A61K 33/20* (2013.01); *A61K 31/19* (2013.01); *A61K 31/194* (2013.01); *A61K 33/06* (2013.01); *A61P 31/04* (2018.01)

(58) Field of Classification Search
CPC ....................................................... A61P 31/04
See application file for complete search history.

(56) References Cited

U.S. PATENT DOCUMENTS 1,542,928 A * 6/1925 Wolff

FOREIGN PATENT DOCUMENTS

| CN | 104430311 A | * 5/2017 | ............ A01N 25/06 |
| ES | 2 315 174 | 3/2009 | |
| ES | 2315174 | 3/2009 | |
| ES | 2315174 B1 | * 10/2009 | ............ A01N 25/12 |

OTHER PUBLICATIONS

ES2315174B1, Google English translation, downloaded in Feb. 2021 (Year: 2021).*
CN104430311A, Google English translation, downloaded in Feb. 2021 (Year: 2021).*
Carlos Estrela, Antimicrobial Effect of 2% Sodium Hypochlorite and 2% Chlorhexidine Tested by Different Methods, Braz Dent J (2003) 14(1): 58-62 (Year: 2003).*
International Search Report for PCT/CN2017/099032 dated May 21, 2018, 6 pages.
Written Opinion of the ISA for PCT/CN2017/099032 dated May 21, 2018, 4 pages.
International Search Report issued in PCT/CN2017/099032, dated May 21, 2018.
Written Opinion issued in PCT/CN2017/099032, dated May 21, 2018.
Chen, H., et al., "Experimental Study on toxicity of Chloramine B Disinfectant," Journal of Preventive Medicine Information, vol. 10, No. 1, pp. 43-44, Jan. 31, 1994. English Abstract only.
Chang, S., "Research Progress on Resistance of Pathogenic Bacteria on Nosocomial Infection to Disinfectants," Chinese Journal of Disinfection, vol. 30, No. 5, pp. 450-455, May 31, 2003. English Abstract only.

* cited by examiner

*Primary Examiner* — Mark V Stevens
*Assistant Examiner* — Alparslan Asan
(74) *Attorney, Agent, or Firm* — Nixon & Vanderhye P.C.

(57) ABSTRACT

A decolonization drug, a preparation method thereof and an application thereof. The decolonization drug is non-antibiotic, simple and convenient to use, and can be used systemically, and has more types of sterilization; The decolonization drug involved in the invention contains added special components, which can improve the bactericidal performance of the drug through the activator effect; The decolonization drug is suitable for use in adults and sensitive populations, including the elderly, pregnant women, infants, children, etc.; especially as a mucosal drug for nasal mucosa, oral mucosa, ocular mucosa, abdominal mucosa, genital mucosa, etc., and can also be used as a bactericidal drug in other medical fields, including diabetic foot, burns, surgical site infections (SSIs), etc.

14 Claims, 1 Drawing Sheet

DE-COLONIZATION DRUG, PREPARATION METHOD THEREFOR, AND APPLICATION THEREOF

This application is the U.S. national phase of International Application No. PCT/CN2017/099032 filed Aug. 25, 2017, the entire contents of which is hereby incorporated by reference.

TECHNICAL FIELD

The invention relates to the field of decolonization drug, and in particular to a decolonization drug, preparation method thereof, and application thereof.

BACKGROUND OF RELATED ART

The nasal cavity is a sinus cavity open to the outside of a human body, and the hospital is a common place for the collection of pathogenic microorganisms. Relevant data show that the nasal cavity of the medical staff who have been working in the hospital for a long time generally show up the phenomenon of colonizing pathogens. The colonization rate is over 60%, and the pathogens colonized in nasal cavity of the medical staff are mainly Staphylococcus epidermidis (52.80%), Staphylococcus haemolyticus (30.84%), Klebsiella pneumoniae (6.54%), Staphylococcus aureus (3.74%) and Enterobacter cloacae (3.27%).

Nasal colonization of Staphylococcus aureus is a risk factor for S. aureus infection in hospitals. For example, a considerable number of patients with methicillin-resistant Staphylococcus aureus (MRSA) colonization will develop MRSA infection, such as pneumonia, soft tissue infection or primary BSI. In adults, the ratio is 18%-33%. The risk of infection in colonized patients is not limited to hospitalization and may extend until after discharged from hospital. A study of patients with MRSA colonization identified during the previous hospitalization found that the risk of MRSA infection was 29% within 18 months of MRSA colonization. Other studies reported that a significant proportion of patients with MRSA infection after discharge were admitted to the hospital.

Among pediatric patients, 8.5% of patients admitted to the hospital on admission were found to have MRSA infection in the future. In addition, 47% of patients who received MRSA colonization during the pediatric ICU developed MRSA infection. In addition, risk factors for MRSA colonization include severe underlying disease or comorbidities, prolonged hospital stay, use of broad-spectrum antibiotics, indwelling invasive devices (such as central venous catheters), and frequent exposure to health care facilities or medical workers.

Targeted target decolonization and general decolonization in the ICU (Intensive Care Unit) are candidates for prevention of health care-associated infections, but for infections caused by resistant strains such as methicillin-resistant Staphylococcus aureus (MRSA), the general decolonization measure are more effective than the decolonization of the target bacteria.

Among them, mupirocin is an antibiotic that inhibits the synthesis of bacterial proteins and RNA. It has excellent antibacterial activity against Streptococcus and Staphylococcus aureus in vitro. Because it is easy to decompose, it is generally not used systemically. Mupirocin is currently the most commonly used drug for the removal of drug-resistant bacteria, especially MRSA, and is usually applied by nasal application.

However, with the widespread application of decolonization strategies in the ICU, the resistance of conventional means such as mupirocin has changed accordingly. Recent studies have shown that the resistance rate of mupirocin is significantly increased, and there are more and more cases of mupirocin failure to decolonize. This is especially evident in patients with multiple sites of MRSA colonization.

Therefore, there is an urgent need for a decolonization drug that can replace or partially replace mupirocin, non-antibiotic, and non-resistance.

Reactive oxychlorine species (ROS-CL, hereinafter referred to as ROCL) is a potent fungicide produced by the neutrophils of the immune system. It is a natural barrier in the body. It is non-antibiotic, no drug resistance mechanism. According to experiments, every $10^6$ in vitro activated neutrophils produce 0.1 um concentration of ROCL. This amount of ROCL can kill $1.5\times 10^7$ E. coli within 5 minutes. Experiments show that ROCL has killing effects against bacteria, viruses, molds, spores, etc.

In addition, magnesium is one of the most abundant cations in the body. It participates in many physiological and chemical processes and plays an important role. It is an activator of various enzymes. For example, alkaline and acid phosphatase, phosphomutase, pyrophosphatase, creatine kinase, hexokinase, leucine aminopeptidase and carboxylase, etc., all of which require the activation of magnesium ions. Magnesium is an essential element in the macromolecular structures of DNA, RNA and ribosomes, and is an important element in maintaining normal nerve function and muscle.

Since high-purity ROCL is usually synthesized by the human autoimmune system itself and due to the unstable nature of ROCL itself, until now, a steady state ROCL-related solution with controlled concentration and purity has not been exploited as a commercial product.

The information disclosed in background part is only intended to enhance an understanding of the general background of the invention, and should not be taken as an acknowledgement or any form of suggestion that this information forms the prior art already known to a person skilled in the art.

SUMMARY OF THE INVENTION

In order to overcome the deficiencies of the prior art, the object of the present invention is to provide a decolonization drug, preparation method thereof, and application thereof. The decolonization drug is non-antibiotic, simple and convenient to use, and can be used systemically and has more types of sterilization.

To achieve the above object, the present invention provides a decolonization drug comprising a ROCL solution, a magnesium chloride solution, and pure water, wherein the ROCL solution is prepared as follows:

Mixing 55 wt %-65 wt % lactic acid with 0.5 wt %-1.5 wt % sodium citrate in a ratio by volume of 1 L:15 L-25 L, mixing 4.5 wt %-5.5 wt % chloramine with USP water in a ratio by volume of 1 L:1450 L-1550 L, then mixing the two mixed solutions in a ratio by volume of 6 L:6.5 L to 7.5 L to prepare the ROCL solution.

In an embodiment of the present invention, the concentration of the ROCL solution is from 0.9 to 3.1%, preferably, the concentration of the ROCL solution is 2%.

In an embodiment of the present invention, the concentration of the magnesium chloride solution is 7 to 9%, preferably, the concentration of the magnesium chloride solution is 8%.

In an embodiment of the present invention, the mass ratio of the ROCL solution to the magnesium chloride solution contained in the decolonization drug is 6-10:1-3, preferably, the mass ratio of the ROCL solution to the magnesium chloride solution contained in the decolonization drug is 7-9:1.5-2.5.

In an embodiment of the present invention, the mass ratio of the pure water and the ROCL solution contained in the decolonization drug is 75-100:6-10, preferably, the mass ratio of the pure water to the ROCL solution contained in the decolonization drug is 80-90:7-9.

The invention also provides a preparation method of the above decolonization drug, which is obtained by adding the magnesium chloride solution to the ROCL solution and pure water, and stirring.

In an embodiment of the present invention, the magnesium chloride solution is added to the ROCL solution and pure water by dropwise manner, preferably, the dropping rate is 0.5-1 liter/min, further preferably, the magnesium chloride solution is prepared by dissolving magnesium chloride in USP.

In an embodiment of the present invention, the agitation speed is 60-70 rpm.

The invention also provides a use of the above decolonization drug in sterilization.

In an embodiment of the present invention, the bacteria include methicillin-resistant *Staphylococcus aureus* (MRSA), methicillin-resistant coagulase-negative staphylococci (MRCNS), methicillin-sensitive *Staphylococcus aureus* (MSSA), ESBLs (extended-spectrum beta-lactamase)-producing *Klebsiella pneumoniae*, *Pseudomonas aeruginosa*, *Escherichia coli*, *Acinetobacter baumannii*, *Enterobacter cloacae*, *Stenotrophomonas maltophilia*, *Candida albicans* and *Candida tropicalis*.

Compared with the prior art, the present invention has the following beneficial effects:

1. A magnesium chloride solution is added to the decolonization drug of the present invention, which can improve the bactericidal performance of the drug by the activator effect;

2. The decolonization drug of the present invention is non-antibiotic, and can replace or partially replace mupirocin, and is a non-resistance decolonization drug;

3. The decolonization drug of the invention is simple and convenient to use, and is suitable for use by adults and sensitive people, more specifically, including the elderly, pregnant women, infants, children, etc.;

4. The decolonization drug of the present invention can be used systemically, and more specifically, even includes eyes, diabetic feet, burn wounds, surgical wounds, etc.;

5. The decolonization drug of the present invention can be especially used as a mucosal drug for nasal mucosa, oral mucosa, ocular mucosa, abdominal mucosa, private mucosa, etc.;

6. The decolonization drug of the present invention has better histocompatibility than the existing simple ROCL solution, and can significantly reduce the stress reaction such as nasal mucosa stimulation in direct contact with the nasal mucosa;

7. The decolonization drug of the present invention overcomes the shortcoming that mupirocin can only de-colonize a few resistant bacteria such as MRSA, and can de-colonize most existing resistant bacteria, more specifically, including Methicillin-resistant *Staphylococcus aureus* (MRSA), methicillin-resistant coagulase-negative staphylococci (MRCNS), methicillin-sensitive *Staphylococcus aureus* (MSSA), ESBLs-producing (extended broad-spectrum beta-lactamase) *Klebsiella pneumoniae*, *Pseudomonas aeruginosa*, *Escherichia coli*, *Acinetobacter baumannii*, *Enterobacter cloacae*, *Stenotrophomonas maltophilia*, *Candida albicans*, *Candida tropicalis*, and the like.

8. The preparation method of the decolonization drug according to the present invention can ensure the stability of the decolonization drug to the greatest extent, and is beneficial to the activation effect of magnesium chloride as a small molecule drug.

DETAILED DESCRIPTION OF THE EMBODIMENTS

Figure 1:
FIG. 1 is an electron micrograph showing interstitial edema and inflammatory cell infiltration of nasal mucosa observed by electron microscopy at 200-fold in Example 5 of the present application.

The specific embodiments of the present invention are described in detail below with reference to the accompanying drawings, but it is understood that the scope of the present invention is not limited by the specific embodiments.

Example 1: Preparation of Decolonization Drugs of the Present Application

The first group: 75 parts of pure water (UPW), 6 parts of 2% concentration of ROCL solution, 1 part of 8% concentration of magnesium chloride solution.

The second group: 85 parts of pure water (UPW), 8 parts of 2% concentration of ROCL solution, 2 parts of 8% concentration of magnesium chloride solution.

The third group: 100 parts of pure water (UPW), 10 parts of 2% concentration of ROCL solution, and 3 parts of 8% concentration of magnesium chloride solution.

The ROCL solution in the above three groups and in the other examples are prepared by the following methods:

60 wt % of lactic acid is mixed with 1 wt % of sodium citrate in a ratio by volume of 1 L:20 L, 5 wt % of chloramine is mixed with USP water in a ratio by volume of 1 L:1500 L, and then the two mixed solutions are further mixed in a ratio by volume of 6 L:7 L to prepare the ROCL solution.

The entire preparation process is carried out by means of a quaternary tubular static mixing manufacturing unit.

Example 2: The Bactericidal Effect of the Decolonization Drugs of the Present Application The following examples demonstrate that the decolonization drugs of the present application are more effective than the use of only ROCL solution, more specifically:

Drug-resistant strains (multi-drug resistant strains) which may be involved in the nasal cavity during the clinical process are selected, and the sterilizing tests are carried out by using the decolonization drugs of the present invention.

Hospital infection bacteria such as Methicillin-resistant *Staphylococcus aureus* (MRSA), methicillin-resistant coagulase-negative staphylococci (MRCNS), methicillin-sensitive *Staphylococcus aureus* (MSSA), ESBLs-producing (extended broad-spectrum beta-lactam) Enzymes of *Klebsiella pneumoniae, Pseudomonas aeruginosa, Escherichia coli, Acinetobacter baumannii, Enterobacter cloacae, Stenotrophomonas maltophilia, Candida albicans*, and *Candida tropicalis* are used as test strains (all of the above test strains are from the Chinese PLA General Hospital), the decolonization drugs of the invention are subjected to suspension quantitative bactericidal test at 20±1° C., and all clinical strains are resistant to two or more types of antibacterial drugs, and are multi-drug resistant strains.

Preparation of the bacterial suspension, the above strains are inoculated on the nutrient agar slant from the blood nutrient agar plate respectively, cultured for about 20 hours, washed with PBS, and the appropriate bacterial liquid is absorbed and turbid to a turbidity of 0.5 Mai's unit (equivalent to $3.0 \times 10^8$ CFU/Ml), diluted with 1% peptone PBS to a bacterial concentration of $10^6$ CFU/ml-$10^7$ CFU/ml, at the same time, PBS is used as $10^1$, $10^2$, $10^3$, $10^4$, and $10^5$-fold dilutions, and $10^4$, $10^5$-fold dilutions of the bacterial suspension are counted as viable bacteria.

Experimental procedure and results: 4.0 ml of each of the three groups of decolonization drugs in the first embodiment of the present application is added to a 1 ml suspension for 60 s, and then the average value of the bactericidal logarithm value (KL) of the three groups of decolonization drugs in Example 1 is calculated, in contrast, only 4.0 ml of the ROCL solution is added to 1 ml of the suspension, and the bactericidal logarithm value (KL) for 60 s is calculated. The comparison results are shown in Table 1:

Conclusion: It can be seen from Table 1 that the bactericidal logarithm value of the decolonization drug used in this application is higher than the bactericidal logarithmic value of the ROCL solution by a logarithm or more, indicating that the bactericidal effect of the decolonization drug of the present application is significantly better than that of the ROCL solution alone.

Example 3 Sensitization of Decolonization Drugs of the Present Application

The following example demonstrates that the decolonization drug of the present application is more effective in reducing or avoiding the occurrence of stress response than the ROCL-only solution, indicating it has better tissue compatibility and tolerance. More specifically:

The structure of the nasal mucosa is very special. There are many large and porous capillaries and abundant lymphatic network under the epithelial cells, and the nasal mucosa area is large. The surface area of the nasal cavity is more than 120 cm². In the process of application, it is necessary to consider the emergency stimulation reaction such as nasal itching or sneezing etc., which is easily caused by direct contact of the nasal decolonization drug with the nasal mucosa, the following test for testing the sensitization effect of the decolonization drug of the present application.

Experimental Materials and Methods

Materials: animals and groups: 20 SD rats, SPF grade, half male and half female, weighing (200±20) g, provided by Tiantan Hospital Medical Experimental Animal Center. The rats are randomly divided into the decolonization drug group (the decolonization drug of the second group in Example 1), the ROCL group (the ROCL solution in Example 1), the saline group, and the blank group, and each group has 5 SD rats.

TABLE 1

Comparison table between the bactericidal effect of the decolonization drug of the present application and the ROCL-only solution

| Experimental group | MRSA (qacA/B negative) | MRSA (qacA/B positive) | MRCNS | MSSA | Klebsiella pneumoniae | Pseudomonas aeruginosa | Escherichia coli |
|---|---|---|---|---|---|---|---|
| The average value of the bactericidal logarithm value (KL) of the three groups of decolonization drugs in Example 1 of the present application | 6.18 | 6.12 | 6.03 | 6.15 | 6.53 | 6.58 | 6.70 |
| bactericidal logarithm value (KL) by using only ROCL solution | 5.10 | 5.22 | 5.00 | 5.12 | 5.25 | 5.35 | 5.45 |

| Experimental group | Acinetobacter baumannii | Enterobacter cloacae | Stenotrophomonas maltophilia | Candida albicans | Candida tropicalis |
|---|---|---|---|---|---|
| The average value of the bactericidal logarithm value (KL) of the three groups of decolonization drugs in Example 1 of the present application | 6.31 | 5.94 | 6.56 | 6.29 | 6.94 |
| bactericidal logarithm value (KL) by using only ROCL solution | 5.25 | 4.68 | 4.95 | 4.85 | 5.10 |

Note:
The bactericidal logarithm value (KL) is the result of subtracting the logarithm (Lg) of the bacterial concentration before and after sterilization. The higher the KL, the stronger the bactericidal ability and the better the bactericidal effect.

Method: The laboratory temperature is between 22° C. and 25° C., and the relative humidity is between 70% and 90%. In addition to the blank group, rats in each group are dosed with 50 μL of the corresponding liquid by pipette through the right nostril daily, and the rats are maintained in the supine position for 1 minute after each administration, which is beneficial to the liquid to fully contact the nasal mucosa of the administration side, reducing the loss of the liquid. Continuous administration for 14 days, the control results are shown in Table 2:

TABLE 2

Comparison of sensitization effects of the decolonization drugs of the present application, ROCL group, saline group and blank group

| Experimental group | Number of animals | Nasal mucosal irritation symptoms (times/each animal. days) | | |
|---|---|---|---|---|
| | | sneezing | Scratching the nose | Head-twitching |
| Decolonization drug group of the present application (the decolonization drug of the second group in Example 1) | 5 | 1.3 | 1.4 | 1.4 |
| ROCL group (ROCL solution in Example 1) | 5 | 2.4 | 2.7 | 2.5 |
| Saline group | 5 | 1.3 | 1.5 | 1.4 |
| Blank group | 5 | 0.2 | 0.4 | 0.3 |

Conclusion: It can be seen from Table 2 that the decolonization drug group and the saline group of the present application have the same degree of stimulation to the nasal mucosa, which is extremely low, and the ROCL is mildly stimulated to the nasal mucosa. It shows that the improved decolonization drug of the present application has better histocompatibility with respect to ROCL solution, and is more suitable for direct contact with nasal mucosa.

At the same time, 14 days after continuous administration, the rats in each group were sacrificed by spine dislocation. The nasal cavity is cut immediately, and the blood clot and mucus are washed with saline. After visual observation, there is no congestion and edema in the nasal mucosa of all 20 rats.

Therefore, the decolonization drug of the present application has better tissue compatibility than the original ROCL solution after compounding the magnesium chloride small molecule drug, and in the process of direct contact with the nasal mucosa, it can significantly reduce the stress response such as nasal mucosa stimulation.

Example 4 Safety Characteristics of the Decolonization Drug of the Present Application (1) Acute Inhalation Toxicity The acute inhalation toxicity of the drug solution is determined in accordance with the requirements of the ISO 10993-11:1996 standard. Aerosols are administered to 5 male and 5 female rats. The dose of the colonization drug (the decolonization drug of the second group in Example 1) of the present application is 2.27 mg/L of air, and the inhalation test is continued for 4 hours through the nose of the mouse.

Conclusion: After 14 days of inhalation testing, observations show no signs of pharmacology or toxicity. All experimental animals perform normally during the study period, and gross autopsy performed at the end of the study show no visible abnormalities. Based on this test, inhalation of the decolonization drug of the present application does not cause toxic effects.

(2) Genotoxicity

The potential genotoxicity of the decolonization drug of this application is evaluated in accordance with the ISO 10993-3:2003 standard. Five male and five female mice tested are intraperitoneally injected with the test article. The dose used is 12.5 mL per kilogram of body weight of the decolonization drug of the present application (the decolonization drug of the second group in Example 1) for 2 consecutive days. After the injection, the general health and adverse reactions of the mice are observed. On the third day, the mice are terminated and the ratio of polychromatic red blood cells is measured:ratio of positive staining red blood cells. In addition, the incidence of micronucleation of polychromatic erythrocytes is examined.

Conclusion: In the study, clinical observations show no signs of toxicity. Microscopic examination of the experimental animal bone marrow smear show that this ratio does not increase in the experimental group and the untreated test group, indicating no induced mutation effect.

(3) Cytotoxicity

Tests are performed in accordance with the ISO 10993-5:1999 standard to determine the potential for cytotoxicity caused by the decolonization drug of the present application.

A filter disc with 0.1 mL of the decolonization drug of the present application (the decolonization drug of the second group in Example 1) is placed on the surface of the agarose and directly covered with a single layer of mouse fibroblasts (L-929). After incubation for 24 h at 37° C. with 5% $CO_2$, the cytotoxic damage on the prepared specimens is observed. The observations are compared with the positive control and negative control samples.

Conclusion: The samples of the decolonization drug of this application does not show any signs of solubilization or toxicity when the positive and negative control groups exhibit the expected results.

Example 5 More Effective Features

The following examples demonstrate the more effective characteristics of the decolonization drug of the present application compared to the traditional decolonization drug (mupirocin), more specifically:

Using the case-control experiment, all newly-increased patients with multi-drug resistant bacteria in the cooperative hospital are selected for a period of time. The hospitalized patients are divided into the control group and the experimental group, and the control group is selected to be applied intranasally with mupirocin for 5 consecutive days and twice daily. The experimental group selects the decolonization drug (the decolonization drug of the second group in Example 1) involved in the present application, and applies the drug twice a day for 3 consecutive days:

Experimental results: There are 66 cases of multi-drug resistant bacteria in the experimental group, including 9 cases of methicillin-resistant *Staphylococcus aureus* (MRSA), which constitute 13.63%. In the control group, 120 cases of multi-drug resistant bacteria occur. Among them, 35 cases of methicillin-resistant *Staphylococcus aureus* (MRSA) constitute a ratio of 29.16%. From the experimental results, it can be seen that under the same conditions, the experimental group can reduce the number of resistant bacteria cases by more than 40% compared with the control group, indicating that the decolonization drug of the present invention has better decolonization effect than the traditional de-colonization drug (mupirocin).

Figure 2:
FIG. 2 is an electron micrograph showing the normal morphology of the nasal mucosa observed by electron microscopy at 200-fold in Example 5 of the present application, without significant interstitial edema or inflammatory cell infiltration.

During the experiment, it can be found by electron microscopy at 200-fold whether mucosa has interstitial edema, inflammatory cell infiltration or surface epithelial cell shedding; it can show by electron microscopy at 6000-fold whether the mitochondria in the glandular epithelial cells are swollen or edema, it can show by electron microscopy at 10000-fold whether the morphology and structure of the ciliated epithelial cells is normal. FIGS. 1 and 2 are the electron microscopic images of the nasal mucosa by electron microscopy at 200-fold. FIG. 1 shows interstitial edema in the mucosa, inflammatory cell infiltration, which leads to edema and congestion; and FIG. 2 shows normal mucosal morphology, no obvious interstitial edema or inflammatory cell infiltration. Experimental results: There are 2 adverse reactions (with edema and hyperemia symptoms) in the control group, as shown in FIG. 1; there is no adverse reaction in the experimental group, as shown in FIG. 2.

Discussion of results: The decolonization drug of the present invention can significantly reduce the incidence of multi-drug resistant bacteria and the incidence of *Staphylococcus aureus* (MRSA), and is more effective than conventional decolonization drugs (mupirocin), and has no adverse reactions.

The foregoing descriptions of specific embodiments of the present invention are presented for purposes of illustration and description. It is not intended to be exhaustive or to limit the invention to the precise form disclosed, and obviously many modifications and variations are possible in light of the above teaching. The exemplary embodiments are chosen and described in order to explain certain principles of the invention and their practical application, to thereby enable others skilled in the art to make and utilize various exemplary embodiments of the present invention, as well as various alternatives and modifications thereof. The invention is to be limited only by the claims provided below and equivalents thereof.

The invention claimed is:

1. A decolonization drug, which comprises a reactive oxychlorine species (ROCL) solution, a magnesium chloride solution and pure water, wherein the ROCL solution is prepared as follows:
   mixing 55-65 wt % lactic acid with 0.5-1.5 wt % sodium citrate in a ratio of lactic acid to sodium citrate by volume of 1 L to 15-25 L to produce a first mixed solution;
   mixing 4.5-5.5 wt % chloramine with pure water in a ratio of chloramine to water by volume of 1 L to 1450-1550 L to produce a second mixed solution; and
   mixing the two mixed solutions in a ratio of the first mixed solution to the second mixed solution by volume of 6 L to 6.5-7.5 L to prepare the ROCL solution; and
   wherein the magnesium chloride is an activator, the mass ratio of the ROCL solution to the magnesium chloride solution contained in the decolonization drug is 6-10 to 1-3, and the concentration of the magnesium chloride in the magnesium chloride solution is from 7 to 9 wt %.

2. The decolonization drug according to claim 1, wherein the concentration of the ROCL solution is from 0.9 to 3.1 wt %.

3. The decolonization drug according to claim 2, wherein the concentration of the ROCL solution is 2 wt %.

4. The decolonization drug according to claim 1, wherein the concentration of the magnesium chloride in the magnesium chloride solution is 8 wt %.

5. The decolonization drug according to claim 1, wherein the mass ratio of the ROCL solution to the magnesium chloride solution contained in the decolonization drug is 7-9 to 1.5-2.5.

6. The decolonization drug according to claim 1, wherein the mass ratio of the pure water to the ROCL solution contained in the decolonization drug is 75-100 to 6-10.

7. The decolonization drug according to claim 6, wherein the mass ratio of the pure water to the ROCL solution contained in the decolonization drug is 80-90 to 7-9.

8. A preparation method of the decolonization drug according to claim 1, comprising:
   adding the magnesium chloride solution to the ROCL solution and pure water, and
   stirring the mixture to obtain the decolonization drug.

9. The preparation method according to claim 8, wherein the magnesium chloride solution is added to the ROCL solution and pure water by dropping.

10. The preparation method according to claim 9, wherein the dropping rate is 0.5-1 liter/min.

11. The preparation method according to claim 9, wherein the magnesium chloride solution is prepared by dissolving magnesium chloride in pure water.

12. The preparation method according to claim 8, wherein the stirring speed is 60-70 rpm.

13. A method of sterilization comprising applying the decolonization drug according to claim 1.

14. The method of sterilization according to claim 13, wherein the decolonization drug kills bacteria, and wherein the bacteria comprises a bacterium selected from the group consisting of methicillin-resistant *Staphylococcus aureus*, methicillin-resistant coagulase-negative staphylococci, methicillin-sensitive *Staphylococcus aureus*, extended-spectrum beta-lactamase-producing *Klebsiella pneumoniae, Pseudomonas aeruginosa, Escherichia coli, Acinetobacter baumannii, Enterobacter cloacae, Stenotrophomonas maltophilia, Candida albicans, Candida tropicalis* and a combination thereof.

\* \* \* \* \*